United States Patent
Dearn et al.

(10) Patent No.: US 7,220,767 B2
(45) Date of Patent: *May 22, 2007

(54) PHARMACEUTICAL FORMULATIONS CONTAINING ZOLMITRIPTAN

(75) Inventors: Alan Roy Dearn, Hertfordshire (GB); Sarah Louise Williamson, Hertfordshire (GB); John Simon Summers, Hertfordshire (GB); Trevor John Coomber, Hertfordshire (GB)

(73) Assignee: AstraZeneca AB, Sodertalje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 10/854,959

(22) Filed: May 27, 2004

(65) Prior Publication Data

US 2004/0214899 A1    Oct. 28, 2004

Related U.S. Application Data

(63) Continuation of application No. 10/129,773, filed as application No. PCT/GB00/04528 on Nov. 28, 2000, now Pat. No. 6,750,237.

(30) Foreign Application Priority Data

Dec. 3, 1999    (GB) ................................ 9928578.5

(51) Int. Cl.
*A01N 43/76* (2006.01)
*C07D 419/00* (2006.01)

(52) U.S. Cl. ..................................... 514/376; 548/122
(58) Field of Classification Search ................ 514/376; 548/122

See application file for complete search history.

(56) References Cited

U.S. PATENT DOCUMENTS 6,750,237 B1 * 6/2004 Dearn et al. ................. 514/376

FOREIGN PATENT DOCUMENTS

| EP | 0 636 623 A1 | 2/1995 |
|---|---|---|
| EP | 636623 | 2/1995 |
| GB | 2 315 673 A | 2/1998 |
| WO | WO 98/02187 | 1/1998 |
| WO | WO-9802186 * | 1/1998 |
| WO | WO 9802186 | 1/1998 |
| WO | WO-98/34595 | 8/1998 |
| WO | WO 98/34595 | 8/1998 |

* cited by examiner

Primary Examiner—Alton Pryor
(74) Attorney, Agent, or Firm—Karen H. Kondrad

(57) ABSTRACT

A pharmaceutical formulation of the 5HT1-agonist, zolmitriptan, for use in intranasal administration. The formulation is useful in treating migraine and related disorders.

16 Claims, No Drawings

PHARMACEUTICAL FORMULATIONS CONTAINING ZOLMITRIPTAN

RELATED APPLICATIONS

This application is a continuation application of U.S. application Ser. No. 10/129,773, filed Aug. 28, 2002 now U.S. Pat. No. 6,750,237, the specification of which is hereby incorporated by reference in its entirety, which is a national stage filing under 35 U.S.C. 371 of PCT application PCT/GB00/04528, filed Nov. 28, 2000, which claims priority from Great Britain Application No. 9928578.5, filed Dec. 3, 1999, the specifications of each of which are herein incorporated by reference in their entireties.

The present invention relates to new pharmaceutical formulations, their preparation and their use in treatment of disease. In particular the present invention relates to pharmaceutical formulations of the anti-migraine drug zolmitriptan for nasal application.

Zolmitriptan has the chemical name (S)-4-{{3-[2-(dimethylaminoethyl]-1H-indol-5-yl]methyl]-2-oxazolidinone. Zolmitriptan is a selective 5HT1-receptor agonist. The 5HT1-receptor mediates vasoconstriction and thus modifies blood flow to the carotid vascular bed. 5HT1-receptor agonists are beneficial in the treatment (including prophylaxis) of disease conditions wherein vasoconstriction in the carotid vascular bed is indicated, for example migraine, cluster headache and headache associated with vascular disorders, hereinafter referred to collectively as 'migraine'. Zolmitriptan has been developed for the acute treatment of migraine in the form of a 2.5 mg and 5 mg tablet intended to be taken up to a maximum of 15 mg per day.

Although zolmitriptan is a successful drug of considerable benefit to migraine sufferers, there is a continuing need for alternative methods for the direct treatment of migraine and the prophylactic treatment of migraine. In particular, patients suffering from migraine or the onset of migraine need fast relief of their suffering.

Zolmitriptan is a member of a class of drugs known as triptans, for example sumatriptan, naratriptan and rizatriptan, which are prescribed for the treatment of migraine. The leader in terms of sales is sumitriptan which has been marketed as an oral formulation. A subcutaneous formulation was also developed; this was more efficacious (P. Tfelt-Hansen, Cephalalgia 1998, Vol 18 (8), page 532–8) and gave a faster onset of action but was not so acceptable to the patient. An intranasal spray was also developed. This was more user-friendly than the subcutaneous injection but was reported to be less effective in reducing the symptoms of migraine attacks (C Dahlof, Cephalalgia 1998; 18 (5): 278–282). Also, many patients reported an unpleasant bitter taste after using the nasal spray.

The present inventors sought a formulation of zolmitriptan that achieved fast relief whilst maintaining high efficacy. They also sought a formulation that, for the wide variety of patients that suffer from migraines, had a more acceptable route of administration than a subcutaneous injection. Clearly, the thought of a subcutaneous injection may dissuade many patients from taking appropriate and necessary treatment. Furthermore, the inventors sought a formulation that was convenient, effective and acceptable to the patient and did not cause any unnecessary irritancy or side-effects.

U.S. Pat. No. 5,466,699 discloses a class of chemical compounds for the treatment and prophylaxis of migraine. U.S. Pat. No. 5,466,699 discloses that this class of compounds may be formulated for oral, sublingual, buccal, parenteral (for example subcutaneous, intramuscular or intraveneous), rectal, topical and intranasal administration and examples of such possible formulations, including an example of an intranasal formulation, are disclosed. The intranasal formulation consists of an active ingredient, methyl hydroxybenzoate (0.2%), propyl hydroxybenzoate (0.02%), citrate buffer and sufficient hydrochloric acid to take the pH to 7.

The present inventors devised an intranasal formulation of zolmitriptan that provided effective and improved fast relief for migraine sufferers. Although, the inventors do not wish to be bound by theory, it is thought that this is at least partly due to the direct mucosal absorption of a significant proportion of zolmitriptan administered by the intranasal route.

Furthermore, studies with an intranasal formulation of zolmitriptan having a pH of above 7.0, at a pH of 7.4, showed the stability of that formulation would not be acceptable over extended periods of time.

The present inventors provided an improved rapid onset of action with a stable intranasal formulation of zolmitriptan having a pH of below 7.0. In addition, this formulation was acceptable to the general patient population and did not cause unnecessary irritancy or side effects.

Accordingly the present inventors provide a pharmaceutical formulation suitable for intranasal administration which comprises zolmitriptan and a pharmaceutically acceptable carrier wherein the pH of the formulation is less than 7.0.

The zolmitriptan formulation for intranasal administration is generally prepared as an aqueous formulation and typically is buffered. Suitable buffering agents include citric acid, phosphates such as disodium phosphate (for example the dodecahydrate, heptahydrate, dihydrate and anhydrous forms) or sodium phosphate and mixtures thereof (for example McIlvaine's buffer which is a mixture of citric acid and disodium phosphate).

In a particular aspect the pH of the pharmaceutical formulation of zolmitriptan is below 6.0, for example in the range 3.5 to 5.5, and in particular in the range 4.5 to 5.5. In a particular aspect the pH of the formulation is about 5.0.

In addition to the buffer, the zolmitriptan formulation may contain other ingredients typically found in intranasal formulations, such as antioxidants for example sodium metabisulphite, taste-masking agents such as menthol and sweetening agents for example dextrose, glycerol, saccharin and sorbitol.

In another aspect the present invention provides an aqueous solution of zolmitriptan in a buffer at a pH of less than 7.0 in particular at a pH below 6.0, for example in the range 3.5 to 5.5 and in particular in the range 4.5 to 5.5, for example at about 5.0. In particular the present invention provides an aqueous solution of zolmitriptan in a buffer of citric acid and phosphate at a pH of less than 7.0, in particular at a pH below 6.0, for example in the range 3.5 to 5.5 and in particular in the range 4.5 to 5.5, for example at about 5.0.

The pharmaceutical formulation of the present invention may be co-administered (simultaneously or sequentially) with one or more pharmaceutical agents of value in treating migraine or related disease conditions.

The pharmaceutical formulations of the invention will normally be administered to humans so that, for example a unit dose of about 0.5 mg to 15 mg (for example 0.5 mg, 1.0 mg, 2.5 mg, 5.0 mg and 10 mg) of zolmitriptan is delivered to the patient in need thereof. The concentration and volume of the formulation may vary as known in the intranasal art, typically a volume of 50 to 250 µl is administered, for example 50 µl or 100 µl (in one spray or in two 50 µl sprays—one for each nostril), The precise dose delivered depends on various factors known in the art including the weight, age and sex of the patient being treated and on the particular migraine disease condition being treated. Such a unit dose may be taken at any stage in the onset of, or during the course of, a migraine attack. Such a unit dose may be taken as needed, typically from 1 to 3 times a day.

The pharmaceutical formulations of this invention may be prepared by dissolving zolmitriptan in an acidic medium, for example aqueous citric acid, thereby forming the citrate salt of zolmitriptan, and taking the pH to the desired value by adding a suitable agent for example a phosphate. The resultant buffered solution is typically manufactured to ensure that it contains a low bioburden or to ensure that it is sterile. Typically the solution is sterilised for example by passing through a sterile filter (for example 0.2 μm) or by autoclaving. Preferably, the solution is purged with nitrogen, and overlaid with nitrogen in the primary pack, to minimise the possibility of degradation. Alternatively, another inert gas, such as argon, could be used. Therefore in another aspect the present invention provides a sterile pharmaceutical formulation suitable for intranasal administration which comprises zolmitriptan and a pharmaceutically acceptable carrier wherein the pH of the formulation is less than 7.0.

The pharmaceutical formulations of the invention are typically filled into a suitable administration device capable of delivering a unit dose amount of zolmitriptan to the patient in need thereof. Such administration devices include those available commercially and the device disclosed in UK Registered Design 2071555. Therefore in a another aspect, the present invention provides an intranasal administration device containing zolmitriptan and a pharmaceutically acceptable carrier wherein the pH of the formulation is less than 7.0.

The filled intranasal administration device may be packaged to provide protection from light. Accordingly in yet a further aspect, the present invention provides an intranasal administration device containing zolmitriptan and a pharmaceutically acceptable carrier in light-protecting packaging, for example in foil pouches. In an alternative aspect, the device itself is a dark colour to provide protection from light, for example, a dark blue colour.

Therefore in a further aspect the present invention provides a pharmaceutical formulation suitable for intranasal administration which comprises zolmitriptan and a pharmaceutically acceptable carrier wherein the pH of the formulation is less than 7.0 for use in a method of therapeutic treatment of the human or animal body.

In yet a further aspect the present invention provides a method of treating a disease condition wherein agonism of 5HT1-receptors is beneficial which comprises administering an effective amount of a pharmaceutical formulation suitable for intranasal administration which comprises zolmitriptan and a pharmaceutically acceptable carrier wherein the pH of the formulation is less than 7.0. The present invention also provides the use of zolmitriptan and a pharmaceutically acceptable carrier in the manufacture of a pharmaceutical formulation suitable for intranasal administration wherein the pH of the formulation is less than 7.0.

Zolmitriptan used in the formulations of the present invention may be prepared according to the disclosures of WO 91/18897 and WO 97/061.62.

EXAMPLES 1–4

Zolmitriptan is dissolved in an aqueous solution of citric acid, 0.4M disodium phosphate dodecahydrate is added to pH 5.0 and water of injection is added to the desired volume. In this manner solutions with concentrations of zolmitriptan of 5 mg/mL, 10 mg/mL, 25 mg/mL and 50 mg/mL are prepared. The solution is filtered through a sterilizing grade filter (0.2 μm), and filled into USP/Ph Eur Type 1 glass vials (nominal spray volume 100 μL) which are closed with chlorobutyl stoppers.

TABLE 1

| Nasal Spray Nominal Strength | 0.5 mg | 1 mg | 2.5 mg | 5 mg |
|---|---|---|---|---|
| Solution Concentration | 5 mg/ml | 10 mg/ml | 25 mg/ml | 50 mg/ml |
| Zolmitriptan | 0.5 | 1.0 | 2.5 | 5.0 |
| Citric acid, anhydrous USP/Ph Eur | 1.11 | 1.29 | 1.79 | 2.60 |
| Disodium phosphate dodecahydrate USP/Ph Eur* | qs to pH 5.0 | qs to pH 5.0 | qs to pH 5.0 | qs to pH 5.0 |
| Water for Injections USP/Ph Eur | to 0.1 ml | to 0.1 ml | to 0.1 ml | to 0.1 ml |

*Added as a 0.4 M solution of Disodium Phosphate Dodecahydrate Ph Eur/USP diluted with purified water USP/Ph Eur.

The vials are assembled into the unit dose nasal spray device disclosed in UK Registered Design 2071555. This device comprises a vial holder, an actuation device and a protection cap. The assembled device may be used to deliver unit doses of zolmitriptan of 0.5 mg, 1.0 mg, 2.5 mg or 5.0 mg in a single administration. The filled nasal spray device is packaged into a plastic tray and placed inside a carton to provide protection from the light.

EXAMPLES 5–8

Zolmitriptan is dissolved in an aqueous solution of citric acid, 0.4M disodium phosphate is added to pH 5.0 and—water of injection is added to the desired volume. In this manner solutions with concentrations of zolmitriptan of 5 mg/mL, 10 mg/mL, 25 mg/mL and 50 mg/mL are prepared. The solution is filtered and filled into USP/Ph Eur Type 1 glass vials (nominal spray volume 100 μL) which are closed with chlorobutyl stoppers.

TABLE 1

| Nasal Spray Nominal Strength | 0.5 mg | 1 mg | 2.5 mg | 5 mg |
|---|---|---|---|---|
| Solution Concentration | 5 mg/ml | 10 mg/ml | 25 mg/ml | 50 mg/ml |
| Zolmitriptan | 0.5 | 1.0 | 2.5 | 5.0 |
| Citric acid, anhydrous USP/Ph Eur | 1.11 | 1.29 | 1.79 | 2.60 |
| Disodium phosphate USP/Ph Eur* | qs to pH 5.0 | qs to pH 5.0 | qs to pH 5.0 | qs to pH 5.0 |
| Purified Water USP/Ph Eur | to 0.1 ml | to 0.1 ml | to 0.1 ml | to 0.1 ml |

*Added as a 0.4 M solution of Disodium Phosphate Ph Eur/USP diluted with purified water for injection.

The vials are autoclaved at 121° C. for 15 minutes. They are then assembled into the unit dose nasal spray device disclosed in UK Registered Design 2071555. This device comprises a vial holder, an actuation device and a protection cap. The assembled device may be used to deliver unit doses of zolmitriptan of 0.5 mg, 1.0 mg, 2.5 mg or 5.0 mg in a single administration. The filled nasal spray device is packaged into a plastic tray and placed inside a carton to provide protection from the light.

EXAMPLE 9

The patient removes the packaging from the nasal spray device, and then removes the protection cap. The patient then inserts the nozzle of the device into a nostril and actuates it to administer a single dose.

The invention claimed is:

1. A pharmaceutical formulation suitable for intranasal administration which comprises zolmitriptan and a pharmaceutically acceptable carrier wherein the pH of the formulation is less than 6.0.

2. A pharmaceutical formulation according to claim 1 wherein the pH of the formulation is in the range 3.5 to 5.5.

3. A pharmaceutical formulation according to claim 1 wherein the formulation is buffered.

4. A pharmaceutical formulation according to claim 2 wherein the formulation is buffered.

5. A pharmaceutical formulation suitable for intranasal administration which comprises zolmitriptan and a pharmaceutically acceptable carrier wherein the pH of the formulation is less than 6.0, wherein the formulation is buffered by a mixture of citric acid and disodium phosphate.

6. A pharmaceutical formulation suitable for intranasal administration which comprises zolmitriptan and a pharmaceutically acceptable carrier wherein the pH of the formulation is in the range 3.5 to 5.5, wherein the formulation is buffered by a mixture of citric acid and disodium phosphate.

7. A pharmaceutical formulation according to claim 1 which is sterile.

8. A pharmaceutical formulation according to claim 2 which is sterile.

9. A pharmaceutical formulation according to claim 3 which is sterile.

10. A pharmaceutical formulation according to claim 4 which is sterile.

11. A pharmaceutical formulation according to claim 5 which is sterile.

12. A pharmaceutical formulation according to claim 6 which is sterile.

13. An intranasal administration device containing a pharmaceutical formulation as defined in any one of claims 1, 2, 6 or 7.

14. An intranasal administration device containing a pharmaceutical formulation as defined in any one of claims 1 to 12 when packaged to provide protection from light.

15. An aqueous solution of zolmitriptan in a buffer at a pH of less than 6.0.

16. The aqueous solution of claim 15, wherein the pH is in the range 3.5 to 5.5.

* * * * *